US000001212H

United States Statutory Invention Registration [19]

[11] Reg. Number: H1212

Thames

[43] Published: Jul. 6, 1993

[54] GENERIC DETECTION WITH A RECEPTOR-BASED FIBER OPTIC SENSOR

[75] Inventor: Kenneth E. Thames, Bel Air, Md.

[73] Assignee: The United States of America as represented by the Secretary of the Army, Washington, D.C.

[21] Appl. No.: 252,429

[22] Filed: Sep. 29, 1988

[51] Int. Cl.[5] ..... G01N 33/566

[52] U.S. Cl. ..... 435/7.8; 436/501; 436/527; 436/546; 436/805; 436/807

[58] Field of Search ..... 436/501, 805, 807; 435/808, 7.21; 422/82.07

[56] References Cited

U.S. PATENT DOCUMENTS

| | | | |
|---|---|---|---|
| H201 | 1/1987 | Yager | 436/151 |
| 4,447,546 | 5/1984 | Hirschfeld | 436/527 |
| 4,789,640 | 12/1988 | Lindstrom | 436/504 |
| 4,950,739 | 8/1990 | Cherksey | 530/350 |

OTHER PUBLICATIONS

Mansouri et al. "A Miniature Optical Glucose Sensor Based on Affinity Binding", *Bio/Technology*, vol. 2, No. 1D, pp. 885–890 (1984).

Angelioes et al. "Functional Unit Size of the Neurotoxin Receptors on the Voltage-Dependent Sodium Channel", *J. Biol. Chem.*, vol. 260, No. 6, pp. 3431–3439 (1985).

Critchley et al. "Interaction of Cholera Toxin with Rat Intestinal Brush Border Membranes," *J. Biol. Chem.*, vol. 256, No. 16, pp. 8724–8731 (1981).

*Primary Examiner*—Robert L. Stoll
*Assistant Examiner*—Joseph D. Anthony
*Attorney, Agent, or Firm*—Anthony T. Lane; Edward Goldberg; Edward F. Costigan

[57] ABSTRACT

The detection of toxins through the use of an optical sensor having a fiber upon which is coupled one or more physiological receptors.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

GENERIC DETECTION WITH A RECEPTOR-BASED FIBER OPTIC SENSOR

FIELD OF USE

This invention relates to an improved method or technique of detecting a class or any one of a number of toxic materials which may be present in fluids on a battlefield.

More particularly, this invention relates to a simple and rapid method of detecting a class or any one of a number of toxins which utilizes a fiber optic sensor whose fiber is coated with a physiological receptor.

BACKGROUND OF INVENTION

The the art, the analysis of fluid suspensions containing toxic materials always required prior knowledge of the specific nature of the material to be detected. This is not always possible. On a battlefield, no one knows what he will encounter.

Further, toxic entities can exist as complex mixtures. It would take many time-consuming steps just to detect what toxic material is present. Rapid detection of the presence of toxic materials is a problem which continues to exist, whenever the battlefield is considered.

Hazard avoidance, or corrective action, could benefit from an assay which indicates the presence of a particular class of toxic materials in fluids. The assay should not have to depend on prior knowledge of the specific nature of the toxic materials encountered in the field.

In the art, U.S. Pat. No. 4,447,546 and U.S. Pat. No. 4,558,014 describe assays of optically dense materials by sampling fluids. However, again, prior knowledge of the specific nature of the toxic material to be identified is necessary. For example, such assays rely on a particular antibody to bind a specific antigen, and vice-versa.

SUMMARY OF INVENTION

It is an object of this invention to provide a simple and rapid method of indicating the presence of toxic materials in fluids on a battlefield.

Another object is to provide a method which requires no special skills or training, and may be used by the ordinary soldier in the field to indicate the presence of toxic materials in fluids.

A further object is to provide a method by which a fiber optic sensor may be used to indicate the presence of a class or any one of a number of toxic materials in the fluids on a battlefield.

Total reflection fluorescence assay coupled with immobilized physological receptors provide the basis of this invention.

PREFERRED EMBODIMENT

In a preferred embodiment, a disposable device is used such as a fiber optic wave guide which consists of a length of precise diameter capillary tubing encasing an approximately axially-disposed optical fiber. The latter fiber has immobilized thereon a functional monolayer of a physiological receptor for the class of toxic materials of interest.

The disposable capillary is provided with a preloaded amount of fluorescently-tagged component to the immobilized receptor. For example, with an immobilized sodium channel receptor on the fiber, a pluality of fluorescently-tagged marine toxin are provided as the preloaded reagent.

In the preferred mode of operation, the preload reagent is bound to the immobilized receptor and is ready for use. At the time of use, a sample of the material to be tested is drawn into the disposable capillary tube having the operational fiber. The sample is allowed to remain for a sufficient period, so as to allow displacement of the tagged preload reagent by the analyte in the sample, and diffusion of these moieties away from the evanescent zone of the analytical fiber.

Observations of the fluorescently-labeled preload reagent are made by total internal reflection fluorescence spectroscopy with one end of the fiber being illuminated and observed. Only that portion of the fluorescent material within the evanescent wave fluoresces, and of this, only that which tunnels back into the fiber is observed. Analyte-dependent release of the preload reagent thus decreases the resident optical signal. This is a displacement procedure. However, for a competitive procedure, see the example which follows:

EXAMPLE

Optical fibers of a convenient diameter and length (0.2-1 mm diameter, 1-2 inches in length) would be activated with a silanization procedure followed by a glutaraldehyde treatment as is well-known in the literature.

Relatively pure receptor, such as the acetylcholine channel receptor, would be prepared in phosphate buffer, ph 7.0, at a concentration of approximately 0.5 mg/ml (milligrams per milliliter).

The activated optical fibers are immersed in the receptor solution and rocked back and forth in order to mix gently at a temperature of 4° C. for approximately 24 hours.

The receptor coated fibers are then placed in a phosphate buffer for storage until use.

For detection purposes a fiber containing the coated receptor for the class of analytes of interest is removed from the phosphate buffer, and mounted in the fiber optic wave guide (FOWG). The buffer is drawn through the FOWG until a sample is introduced.

A small volume of sample (approximately 0.1 ml), along with an accurate amount of fluorescein-labeled toxin representing the class of toxin to be detected, is injected into the flow cell of the FOWG. The sample is allowed to stand in order to undergo a competitive binding for the sites on the receptor which is immobilized on the optical fiber. The fluorescence signal with this particular configuration is inversely proportional to the amount of toxin present in the sample. The concentration of the toxin would be determined by comparing the fluorescence with a standard curve. Other assay configurations, displacement, sandwich, and inhibition may be used depending upon the analyte being detected.

This procedure can be used for one or more particular binding site on a physiological receptor or can be used with multiple binding sites on a given physiological receptor.

The physiological receptors that can be used are varied, and many have been characterized in the open literature. The important point is that the total number of different physiological receptors required are few in number, and can be specified for the class of toxic materials of interest. The methods of the present invention, however, are not to be limited to the pure intact isolated receptors, but to receptors, both natural and artificially produced, used singly or in combination for multiple analyte assays. For example, the sodium channel receptor isolated from the nervous system has been identified as having 5 different binding sites. Table I shows some of the more well-known toxins which bind to this receptor. Different classes of toxins bind to the different receptor sites. It is to be understood that there are many other toxins of interest which bind to the sodium channel receptor as is well-known in the literature.

TABLE I

NEUROTOXIN RECEPTOR SITES ASSOCIATED WITH THE SODIUM CHANNEL RECEPTOR

| RECEPTOR SITE | LIGANDS |
|---|---|
| 1 | Tetrodotoxin, Saxitoxin |
| 2 | Veratridine, Batrachotoxin Aconitine, Grayanotoxin |
| 3 | Alpha-Scorpion Toxins, Sea Anemone Toxins |
| 4 | Beta-Scorpions Toxins |
| 5 | Brevetoxin |

It is likely that other physiological receptors have binding sites which are specific for different classes of ligands.

A second receptor of interest is the Acetylcholine receptor. This physiological receptor binds snake venoms, such as Alpha-Bungarotoxin and Alpha-Cobra toxin.

A third receptor of interest is the calcium channel physiological receptor. This receptor binds several mycotoxins, and some small toxic organophosphate compounds of interest. A fourth class of receptors of interest are the Gangliosides. These receptors bind Ricin, Tetanus, and Cholera, among other toxins. A fifth receptor of interest is Gamma Aminobutyric Acid (GABA) and this binds Diazepan, Picrotoxin, and Quinoline.

All the foregoing physiological receptors are prepared for use in the same manner as is set forth in the foregoing example for both fiber preparation and detection purposes.

ALTERNATES

In an alternate mode of operation, the tagged preload reagents are affixed to the wall of the capillary by entrapment in an appropriate matrix for subsequent release to the sample, or otherwise furnished in known concentration to the sample volume. Thus, upon introducing the sample to the optical fiber coated with immobilized receptors, the preload reagent competes with specific ligand present in the sample for receptor binding sites. Observations of the fluorescently-labeled preload reagent which binds to the fiber are made by total internal reflection fluorescence spectroscopy, as heretofore described. In this instance, the presence of analyte in the sample again results in a decreased optical signal relative to a blank reference.

Detection of materials containing intrinsic fluorescence, such as various protein toxins, may be effected by a third mode of operation. In this case, the preload reagent is not required and binding of analyte is measured directly by monitoring increases in the total internal reflection fluorescence.

The methods of the present invention are not constrained to implementation with a single receptor type coating the optical fiber surface. Screening for any of a number of analytes can be affected, as easily as single analyte testing, by incorporating several different receptors, or receptors in conjunction with other recognition elements on the surface of the same fiber. Also, the various preloaded components of the assay can, on the one hand, all be labeled with the same fluorescent compound, thereby simplifying and optics and detection requirements of the method. On the other hand, more refined appraisals of the type of agent detected can be obtained by increasing the repertoire of optically-active chromophores used to label the different preload reagents. In the latter case, each fluorescent tag would have to be excited and measured at its characteristic wave lengths.

In a similar fashion, groups of different receptors, or receptors in conjunction with other recognition elements, can be immobilized and employed as a recognition surface. Transduction of a selective binding event, in this instance, would be affected by an optically-based detector, such as the optical fiber sensor. Generation of an optical signal could be by displacement of a labeled preload reagent, as discussed above, or by competitive binding with tagged standards.

The methods of the present invention, however, are not limited to the analysis of toxic materials. This technique can be extended to quantitate pathogens, cells, cell fragments, hormones, alkaloids, steroids, therapeutic and pharmacologic agents. Further, a continuous flow cell of proper geometry can replace the disposable capillary tube with axially-placed optical fiber.

In conclusion, since the assay of the present invention contains the necessary reagents in the required quantity and dilution, and since its construction controls the total volume sampled, little skill or training is required for the operator performing the assay. Further, inasmuch as small quantities of physiological receptors can fluorescently-tagged complementary reagents will be required for an assay. Also, since the coating and loading of inexpensive fiber may be easily controlled during manufacture, it will be appreciated that the assay hardware of the present invention may be fabricated reasonably inexpensively.

What is claimed is:

1. A method of detecting a class of toxins in fluids on a battlefield by coating a fiber of an optical sensor with a physiological receptor having multiple binding sites for any one of a number of toxins of a class, contacting said sites with said toxins having fluorescent labels, exciting said fiber to emit a 1st signal, detecting said 1st signal, exposing said contacted fiber to said fluid, exciting said fiber to emit a 2nd signal, and detecting said 2nd signal, comparing said signals for a difference.

2. The method of detecting of claim 1, wherein said physiological receptor is a sodium-channel receptor.

3. The method of detecting of claim 1, wherein said physiological is an acetylcholine receptor.

4. The method of detecting of claim 1, wherein said physiological receptor is a calcium-channel receptor.

5. The method of detecting of claim 1, wherein said physiological receptor is a ganglioslides receptor.

6. The method of detecting of claim 1, wherein said physiological receptor is a gamma aminobutyric acid (GABA) receptor.

* * * * *